(12) United States Patent
Gay et al.

(10) Patent No.: US 9,274,002 B2
(45) Date of Patent: Mar. 1, 2016

(54) METHOD FOR THE NON-DESTRUCTIVE INSPECTION OF AN ORGANIC-MATRIX COMPOSITE MATERIAL

(71) Applicant: AIRCELLE, Gonfreville L'Orcher (FR)

(72) Inventors: Lionel Gay, Le Havre (FR); Thibaud Chopard, Epouville (FR); Odile Lefeu, La Remuee (FR); Frédéric Joubert, Le Havre (FR)

(73) Assignee: AIRCELLE, Gonfreville l'Orcher (FR)

(*) Notice: Subject to any disclaimer, the term of this patent is extended or adjusted under 35 U.S.C. 154(b) by 0 days.

(21) Appl. No.: 14/245,816

(22) Filed: Apr. 4, 2014

(65) Prior Publication Data

US 2014/0217290 A1    Aug. 7, 2014

Related U.S. Application Data

(63) Continuation of application No. PCT/FR2012/052217, filed on Oct. 1, 2012.

(51) Int. Cl.
*G01N 21/35* (2014.01)
*G01N 21/3563* (2014.01)
*G01J 3/45* (2006.01)
*G01N 21/95* (2006.01)
*G01N 29/04* (2006.01)
*G01N 29/12* (2006.01)
*G01N 21/84* (2006.01)

(52) U.S. Cl.
CPC ............ *G01J 3/45* (2013.01); *G01N 21/3563* (2013.01); *G01N 21/95* (2013.01); *G01N 29/041* (2013.01); *G01N 29/12* (2013.01); *G01N 2021/3595* (2013.01); *G01N 2021/8472* (2013.01); *G01N 2201/0221* (2013.01); *G01N 2291/0231* (2013.01); *G01N 2291/2694* (2013.01)

(58) Field of Classification Search
CPC .......................... G01N 21/35; G01N 21/3563
See application file for complete search history.

(56) References Cited

U.S. PATENT DOCUMENTS

| | | | |
|---|---|---|---|
| 7,516,663 B2* | 4/2009 | Ringermacher et al. | 73/601 |
| 2003/0106376 A1* | 6/2003 | Shirzad et al. | 73/606 |
| 2006/0043303 A1 | 3/2006 | Safai et al. | |
| 2008/0137105 A1* | 6/2008 | Howard et al. | 356/630 |
| 2008/0291465 A1* | 11/2008 | Lorraine et al. | 356/502 |
| 2008/0307886 A1* | 12/2008 | Marsh et al. | 73/601 |
| 2009/0133501 A1 | 5/2009 | Georgeson | |
| 2010/0032571 A1* | 2/2010 | Shelley et al. | 250/341.8 |
| 2010/0276578 A1 | 11/2010 | Shelley et al. | |
| 2014/0096350 A1* | 4/2014 | Denton et al. | 29/407.04 |
| 2014/0210997 A1* | 7/2014 | Blanchard et al. | 348/128 |

OTHER PUBLICATIONS

International Search Report issued Nov. 13, 2012 in International Application No. PCT/FR2012/052217.
N. Avdelidis et al., "A study of active thermography approaches for the non-destructive testing and evaluation of aerospace structures", Proc. of SPIE, vol. 6936, pp. 693918-1 to 693918-6.

* cited by examiner

*Primary Examiner* — Christine Sung
(74) *Attorney, Agent, or Firm* — Brinks Gilson & Lione

(57) ABSTRACT

A method for the non-destructive inspection of a part made from an organic-matrix composite material (CMO) includes the steps of: a) carrying out a surface inspection of the part by Fourier transform infrared spectroscopy (FTIS), b) if step a) reveals a defect, carrying out in-depth inspections of the organic-matrix composite material according to two complementary ultrasound techniques.

7 Claims, 1 Drawing Sheet

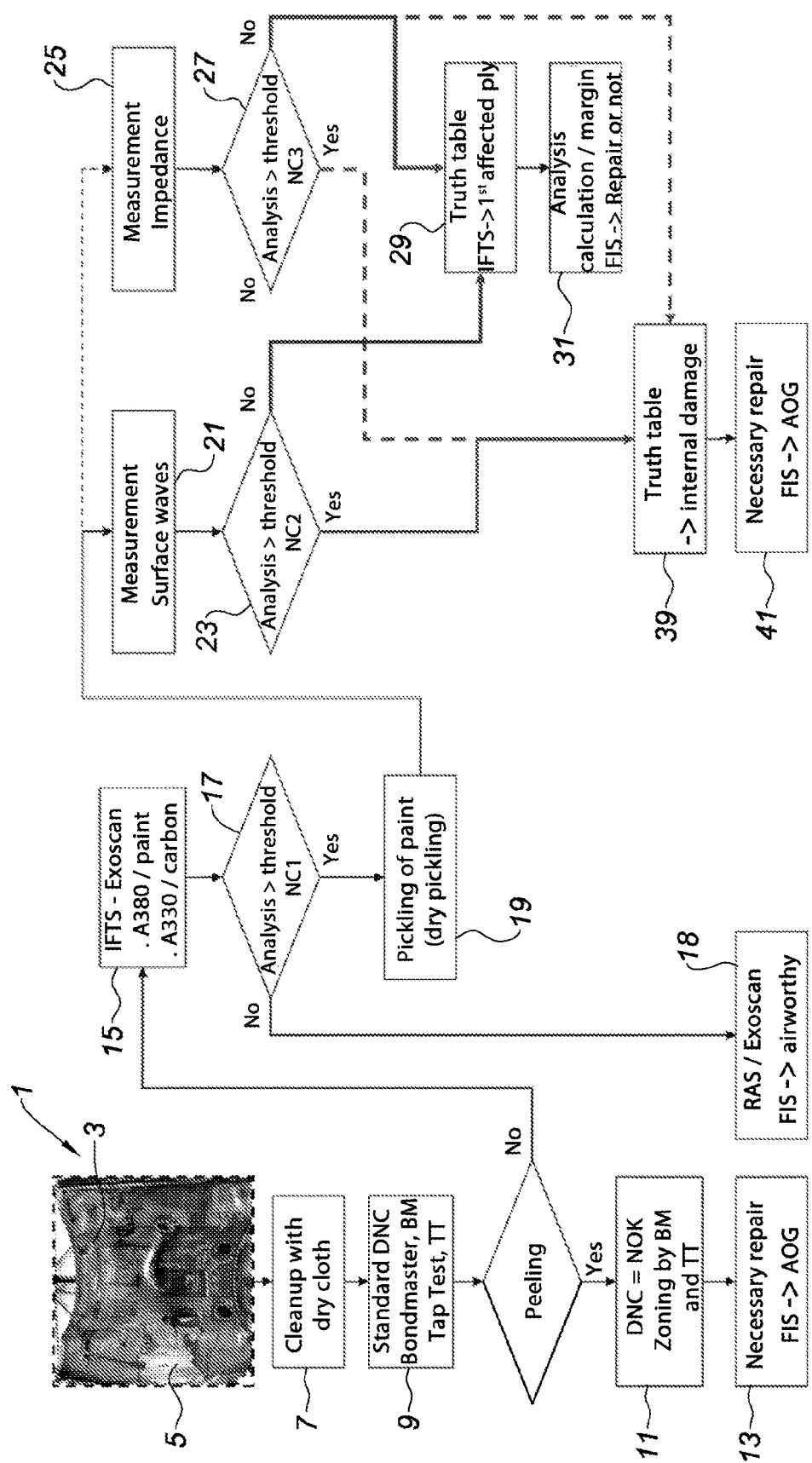

METHOD FOR THE NON-DESTRUCTIVE INSPECTION OF AN ORGANIC-MATRIX COMPOSITE MATERIAL

CROSS-REFERENCE TO RELATED APPLICATIONS

This application is a continuation of International Application No. PCT/FR2012/052217, filed on Oct. 1, 2012, which claims the benefit of FR 11/03022, filed on Oct. 5, 2011. The disclosures of the above applications are incorporated herein by reference.

FIELD

The present disclosure relates to a method of non-destructive inspection (hereinafter, NDI) of an organic-matrix composite material.

BACKGROUND

The statements in this section merely provide background information related to the present disclosure and may not constitute prior art.

Organic-matrix composite materials can be particularly used in the field of aeronautics, and more particularly within a propulsion group comprising a nacelle and, inside the latter, a turbojet.

A particular use of an organic-matrix composite material (hereinafter, OMC) is the production of an internal fixed structure (hereinafter, IFS) designed for careening the turbojet and for defining the secondary flow vein (also known as cold airflow vein) of the turbojet.

Such IFS is subject to very high temperatures on the side of the turbojet, which can eventually lead to deterioration of the OMC by physicochemical aging. Detection of this deterioration should be accomplished as quickly and as simply as possible during maintenance operations.

SUMMARY

The present disclosure is to provide a more reliable and easy to implement method for non-destructively inspecting an OMC part which could be particularly used within an aircraft propulsion system.

The present disclosure provides an NDI method of an OMC part, comprising the steps of:
  a) carrying out a surface inspection of this part by infrared Fourier transform spectroscopy (IFTS);
  if step a) reveals a defect, carrying out in depth inspection of said material according to two complementary ultrasound techniques.

The IFTS surface inspection is easy to implement, and the method according to the present disclosure makes it possible to easily distinguish between favorable instances where no additional inspection is required, and those where more in depth inspection by means of ultrasound techniques is required to remove all doubt (hereinafter, RAD).

For the latter instances, using two complementary ultrasound techniques makes it possible to obtain improvement in reliability and reproducibility of the method.

According to other features of the method in accordance with the present disclosure, which may be taken singly or in combination:
  to implement step a), an average of several IFTS spectra obtained in the examined area is carried out to then move to step b) when the analysis of peaks featuring the physicochemical aging exceeds at least a predetermined, so-called non-conformity threshold, taking into account the paint thickness measurement of the part when the latter is painted;
  to implement step b), the results of the measurements given by each ultrasound technique are collected, and when at least one of these results exceeds a predetermined, so-called non-conformity threshold, it is decided that the part needs to be repaired; such a threshold is defined from decision-support truth tables, the latter being built during development testing;
  the measurements given by each ultrasound technique with a visual analysis based on comparative colorimetric of concerned areas are completed;
  one of the two ultrasound techniques consists is a measurement of acoustic energy transmitted by surface waves on the examined area, and the other of the two ultrasound techniques is a measurement of electromechanical impedance of said area of the material;
  said ultrasound measurements are carried out after a normalization step of said area: this normalization step makes it possible to calibrate the measurements;
  prior to step b), a pickling of the paint layer covering the surface of said part is carried out: this step, only applicable when the part to be inspected is covered with paint, is necessary to implement the ultrasound measurements of step b);
  surface inspection is accompanied with infrared Fourier transform spectroscopy by measuring paint thickness when the part is painted.

The present disclosure is particularly intended for an NDI of a piece of an aircraft propulsion group such as an internal fixed structure (IFS) of an aircraft turbojet nacelle.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawing, in which:

FIG. 1 represents a part to be inspected.

The drawing described herein is for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the chosen example, the part 1 is an IFS, that is, a part designed to careen an aircraft turbojet, comprising at its internal side, that is, on the surface thereof facing the turbojet, a heat insulating layer 3.

In an area 5 of the IFS, the heat insulating layer 3 has been partially cut away, thereby exposing the composite material forming this IFS.

In the context of the presents present disclosure, the composite material is an organic matrix composite (OMC), that is, a composite material formed of a stack of plies each obtained by polymerization of an organic resin (a BNI type resin for example), this resin enclosing, for instance, carbon fibers.

In the example illustrated, area 5 in which the heat insulating layer 3 has been partially cut away, is the OMC material to be inspected.

In fact, this material is subject to very high temperatures, that may lead to defects like OMC deterioration by physico-chemical aging and it is important to periodically test the aging thereof.

At first, the area 5 is cleaned up with a dry cloth (step 7), in order to remove grease and other polluting particles.

Then, a standard DNC is performed (step 9) typically comprising a gluing test, with a Bondmaster (ultrasounds machine specific to this use, available from Olympus) and a Tap Test, that is, a hammer based acoustic test, making it possible to detect potential areas of peeling of the OMC.

If the DNC of step 9 is positive, in step 11 the size of the defected area is determined.

At the end of all these measurements, the magnitude of the necessary repairs for the IFS is known, given that the aircraft will not be able to fly as long as the necessary repairs are not carried out (the initials AOG on the scheme attached hereto refer to "Airplane On Ground", meaning that the aircraft cannot fly).

If with the standard tests carried out in step 9 it is not possible to spot a clear peeling of the OMC, then it is proceeded to step 15, in which a surface inspection of the area 5 of the OMC is carried out, by means of an infrared Fourier transform spectroscopy (IFTS) apparatus.

Such apparatus is available from A2 TECHNOLOGIES under brand name EXOSCAN.

This handheld apparatus has the form of a pistol that is swept over area 5.

This apparatus makes it possible to measure, over surfaces of about 2 mm*2 mm, the absorbance of infrared rays within a wavelength range of 4000 to 500 cm-1.

The absorbance variations of infrared rays reveal the OMC surface defects.

More specifically, several measurement series are carried out by means of the IFTS apparatus in the area 5, then, the obtained spectra are averaged before their utilization.

When the analysis of the peaks featuring the physico-chemical aging (determined by the development testing) is lower than a non-conformity threshold NC1 (step 17), provided consistency with the paint thickness measurement when the part is painted, the OMC is considered free from surface defects, and it is not necessary to carry out further investigations: the conclusion is that the IFS is airworthy (step 18).

When on the contrary, this predetermined threshold NC1 is exceeded, it should be considered that in depth measurements of the OMC need to be carried out in order to characterize, accurately, the nature of the defect.

It should be noted that the internal surface of the IFS 1 may be painted, as is the case with the Airbus A380, or may be exposed, as is the case for instance with the Airbus A330.

When the internal surface of the IFS 1 is painted, it is necessary to perform a dry pickling of the paint layer before any further complementary measures, as is shown in FIG. 19.

This is done in order to avoid interference of the paint, the layer of which typically measures about 40 to 80 microns, with the ultrasound measures that will be detailed below.

As it is obvious on the scheme attached hereto, two series of distinct and complementary ultrasound measurements are carried out in parallel.

At the first ultrasound measurement 21, ultrasound waves are projected onto the surface of the examined area 5 with a certain incidence angle and to thereby generate surface waves so that the energy transmitted by the OMC between the emitter and the receiver is then measured.

More precisely, the surface of the area 5 to be examined is solicited mechanically by means of two transducers, namely an emitter (subjected to oscillatory voltage), and a (passive) receiver.

Practically, the transducers are placed symmetrically relative to a plan normal to the area 5 to be examined, and the amplitude of the ultrasound wave transmitted by the surface waves is measured.

The pair emitter/receiver is displaced around the defected area.

When the measured amounts do not exceed a predetermined non-conformity threshold NC2 (step 23), it is concluded that the test is positive, that is, the OMC exhibits in depth damage.

This first ultrasound measurement series make it possible to characterize the presence of in depth damage in the OMC, when the threshold NC2 is exceeded.

At the second ultrasound measurement series 25, the electromechanical impedance of the examined area 5 of the OMC is determined.

The relationship between the intensity passing through this transducer and the voltage to which it is submitted makes it possible to deduct the electromechanical impedance sought.

Then, the impedance resulting from this ultrasound measurement is compared to a conformity threshold NC3 (step 27).

Typically, the examined area 5 is solicited by means of wave trains the frequency of which ranges between 3 and 7 megahertz.

More precisely, the test logic, according to the results obtained by each of the ultrasound measurement series aforementioned, is the following, being noted that the solid and dotted lines connecting steps 23 and 27 to steps 29 and 39 set no hierarchy between the different possible options: different lines were only used for the sake of clarity.

When the measurements 21 and 25 lead to negative results, in other words, when these measurements remain lower than the thresholds NC2 and NC3, respectively, it is deduced that the OMC is only superficially affected: only the surface ply of the composite is damaged (step 29).

In this case, it may be decided or not to have the IFS repaired (step 31), and therefore to keep the aircraft grounded or not.

This decision depends on other external parameters, such as technical parameters (level of mechanical stress on the area concerned) and financial ones especially related to the remaining life span of the IFS, and these parameters will not be detailed herein.

On the other hand, when at least one of these two measurement series 21, 25 yields a positive testing, it can be deduced that the OMC exhibits internal damage, and that it is therefore necessary to repair the IFS, thus, grounding the aircraft.

More precisely, a situation 39 may be faced where only one of the ultrasound tests 21, 25 is positive, which means that there are actually two positive DNCs, namely, the IFTS test and the wave surface ultrasound test, leading to a grounding of the aircraft (step 41).

Or the two ultrasound tests 21, 25 are positive which means that there are three positive non-destructive tests (step 39: the IFTS test+the two ultrasound tests 21, 25), leading to the repair of the IFS, and therefore the grounding of the aircraft.

The evaluation of the deterioration level of the OMC is made thanks to the truth tables (decision support) which have been established by correlation with the development tests.

As it is understood from the reading of the preceding description, the process according to the present disclosure makes it possible to rapidly and highly reliably detect the deterioration of the material by physicochemical aging on the surface and inside a part made of OMC.

This process makes it possible to set a reproducible and rational operational mode, in which visual and acoustic standard tests are started withy, followed, if need be, by surface measurements carried out very rapidly by means of an IFTS apparatus, these being followed, if need be, by further ultrasound-based measurements.

Each step is only implemented once the precedent step indicates the necessity to proceed, thus preventing the operator from carrying out unnecessary measurements.

This process according to the present disclosure makes it possible to gradually characterize the detected defects, starting at first by surface defects, then, by analyzing the internal structure of the OMC.

The process according to the present disclosure will be easily implemented by operators in charge of the maintenance of aircraft propulsion systems, either during routine checkups, or during specific checkups subsequent to detected incidents.

The present disclosure is in no way limited to the form described and illustrated, given as a way of example.

What is claimed is:

1. A non-destructive inspection method of an area of an organic-matrix composite material (OMC) part, comprising the steps of:
   a) carrying out a surface inspection of said area of the part by means of an infrared Fourier transform spectroscopy (IFTS);
   b) if step a) reveals a defect, carrying out in depth inspections of said organic-matrix composite material according to two different ultrasound techniques.

2. The non-destructive inspection method according to claim 1, wherein for an implementation of step a), several spectra performed in the area inspected are averaged, and when analyzed peaks characterizing a physicochemical aging exceed a predetermined non-conformity threshold (NC1), step b) is carried out.

3. The non-destructive inspection method according to claim 1, wherein, for an implementation of step b), measurement results given by each ultrasound technique are collected, and when at least one of said measurement results exceeds a predetermined non-conformity threshold (NC2, NC3), determining that the area needs to be repaired.

4. The non-destructive inspection method according to claim 3, wherein the measurement results given by each ultrasound technique are completed with a visual analysis based on a comparative colorimetry of the area inspected.

5. The non-destructive inspection method according to claim 1, wherein one of the two ultrasound techniques is a measure of an acoustic energy transmitted by surface waves on the area inspected, and the other one of the two ultrasound techniques is a measure of an electromechanical impedance of said area of the organic-matrix composite material.

6. The non-destructive inspection method according to claim 1, wherein, prior to step b), a pickling of a paint covering a surface of said area is carried out.

7. The non-destructive inspection method according to claim 1, wherein, the infrared Fourier transform spectroscopy (IFTS) is accompanied by a measure of paint thickness when said area is painted.

* * * * *